United States Patent
Nakaichi et al.

(10) Patent No.: US 6,319,195 B1
(45) Date of Patent: Nov. 20, 2001

(54) ENDOSCOPE

(75) Inventors: Katsumi Nakaichi; Shinji Yamamori; Yoshitsugu Yamada, all of Tokyo (JP)

(73) Assignee: Nihon Kohden Corporation, Tokyo (JP)

(*) Notice: Subject to any disclaimer, the term of this patent is extended or adjusted under 35 U.S.C. 154(b) by 0 days.

(21) Appl. No.: 09/421,395

(22) Filed: Oct. 20, 1999

(30) Foreign Application Priority Data

Oct. 20, 1998 (JP) ................................. 10-298138
Nov. 6, 1998 (JP) ................................. 10-316277
Nov. 10, 1998 (JP) ................................. 10-318617

(51) Int. Cl.[7] ............................. A61B 1/00; A61M 16/00
(52) U.S. Cl. ......................... 600/120; 600/146; 600/150
(58) Field of Search ................................. 600/120, 146, 600/150, 194, 197, 188; 604/95.04, 510, 528; 128/200.26

(56) References Cited

U.S. PATENT DOCUMENTS

| 4,529,400 | 7/1985 | Scholten ............................. 604/95 |
| 4,742,819 | * 5/1988 | George ............................. 600/120 |
| 4,921,482 | * 5/1990 | Hammerslag et al. ........... 604/95.04 |
| 5,394,865 | 3/1995 | Salerno . |
| 5,531,686 | * 7/1996 | Lundquist et al. ............... 604/95.04 |
| 5,791,338 | * 8/1998 | Merchant ......................... 128/200.26 |
| 5,941,816 | 8/1999 | Barthel et al. . |

FOREIGN PATENT DOCUMENTS 9-238897   9/1997   (JP) ................................. A61B/1/00

* cited by examiner

*Primary Examiner*—John Mulcahy
(74) *Attorney, Agent, or Firm*—Sughrue, Mion, Zinn, Macpeak & Seas, PLLC

(57) ABSTRACT

An endoscope for intubating an endotracheal tube includes an elongated insertion portion including at least an image transmitting optical fiber bundle, an illumination light transmitting optical fiber bundle, and a bendable element, an operation portion connected to the proximal end portion of the insertion portion, a bending operation mechanism provided in the operation portion, an endotracheal tube connection section provided in the vicinity of a joint between the insertion portion and the operation portion; and a bendable element for bending the insertion portion provided so as to extend from the inside of the insertion portion to the bending operation mechanism.

5 Claims, 4 Drawing Sheets

ENDOSCOPE

BACKGROUND OF INVENTION

1. Field of Invention

The present invention relates to an endoscope for intubating an endotracheal tube which enables optical observation of a patient's body cavity so that an operator can easily intubate the endotracheal tube into a patient who suffers from difficulty in breathing because of a sudden onset of a disease or an injury at the scene of an accident, disaster, or a like occurrence and whose airway must be ensured urgently. More specifically, the present invention relates to the structure of a bending operation section of a portable endoscope for intubating an endotracheal tube, and the endoscope as well enables use of a light source or a power source in combination therewith so as to enable immediate medical response at the scene of an accident or disaster. More specifically, the present invention relates to the structure of an operation portion of a portable endoscope for intubating an endotracheal tube.

2. Related art

A conventionally-practiced method for intubating an endotracheal tube into a patient's body comprises a step of inserting a stylet or an endoscope, which has a bending function, into the internal space of an endotracheal tube and fixing the thus-inserted stylet or endoscope; and a step of intubating the endotracheal tube into the patient's body and guiding the distal end of the endotracheal tube to the larynx by the bending function of the stylet or endoscope, or a step of intubating an endotracheal tube into a trachea while the stylet or endoscope is used as a guide, after direct visual checking of the trachea, and retaining the thus-intubated endotracheal tube in place. One example of the stylet is described in U.S. Pat. No. 4,529,400, and one example of the endoscope is described in Japanese Patent Application Laid-Open No. Hei-9-238897.

In practice, these devices encounter various problems in use. One of the problems is that an operator cannot directly and manually feel the resistance against the endotracheal tube when being intubated into the human body.

In this type of medical device, an insertion portion of the stylet or endoscope is inserted into the internal space of the endotracheal tube, and the insertion portion of the stylet or endoscope is intubated into the human body while being fixed with the endotracheal tube. In the conventional device, a bending operation piece, such as a bending leer or knob, of a bending operation mechanism is provided at a position where the operation piece is to be actuated by the hand that is holding the operation section of the stylet or endoscope. If an attempt is made to hold the endotracheal tube directly by hand, the operator cannot perform a bending operation. For this reason, the operator must intubate the endotracheal tube while holding the operation section. The endotracheal tube has flexibility, whereas the operation section of the stylet or endoscope is rigid. Even if the endotracheal tube is fixedly attached to the stylet or endoscope, the operator cannot feel subtle resistance against the endotracheal tube while being intubated into the patient's body, by way of the hand that is holding the operation section. For this reason, there exists a danger of damaging the wall of a body cavity by forceful intubation of the endotracheal tube.

The operator intubates the endotracheal tube into the patient's body by holding a laryngoscope in, for example, the left hand, to thereby forcefully open the mouth, and by inserting the endotracheal tube equipped with the stylet or endoscope by the right hand while holding the operation section of the stylet or endoscope.

When the endotracheal tube can be inserted by a short distance into the trachea, only the stylet or endoscope is withdrawn. If the stylet or endoscope remains within the endotracheal tube, the entire endotracheal tube has high rigidity. If the endotracheal tube is intubated, exactly as is, the wall of the body cavity may be damaged. For this reason, the rigidity of the endotracheal tube is diminished by only the endotracheal tube being left in the trachea.

Since the endotracheal tube is situated a short distance inside the trachea, it will be forced out by the tongue unless the previously-described operations are performed while the tongue is lifted up by the laryngoscope. Therefore, the operator's left hand is occupied with lifting up the tongue, and only his right hand is available. However, if the operator attempts to lift up the tongue with his right hand, he must release his right hand from the operation section of the stylet or endoscope and hold the endotracheal tube.

If the hand is released from the operation section, the operation section will fall under its own weight and the entire endotracheal tube will be pulled out from the trachea. In order to avoid this, the operator must shift his hand while an assistant supports the endotracheal tube or the operation section. These operations involve stationary and fixed supporting of the endotracheal tube. If shifting of the hand fails for poor coordinated operation or the endotracheal tube is moved during the shifting of the hand, the endotracheal tube is pulled out from the trachea.

Further, in practice, the intubating operation in connection with this method involves various problems. One of the problems is that the length of the insertion portion changes when the endoscope is bent. According to the conventional method, the endoscope is usually intubated into the patient's body while the distal end of the endoscope remains a slight distance short of the distal end of the endotracheal tube. In many cases, the endoscope is to be used for a patient whose larynx is bleeding because of injury. In such a case, if the endoscope is intubated together with the endotracheal tube while the distal end of the endoscope sticks out from the distal end of the endotracheal tube, an objective lens attached to the distal end of the endoscope is stained with blood and becomes unable to acquire images. However, if the endoscope remains far short of the distal end of the endotracheal tube, the interior wall of the endotracheal tube occupies the field of view of the endoscope, thus limiting the field of view of the operator and preventing the operator from acquiring a wide-range view of the trachea. Accordingly, the operator encounters difficulty in searching an area of interest. For these reasons, the distal end of the endoscope is set in the manner as mentioned above; the distal end of the endoscope remains a slight distance short of the distal end of the endotracheal tube such that the interior wall of the endotracheal tube does not appear within the field of view of the endoscope.

Since the endotracheal tube is sturdy, a considerable amount of force is required to bend the endoscope during intubation of the endotracheal tube. For this reason, the endoscope has a structure which is relatively sturdy and enables strong bending action. In one example of such a structure, an insertion portion is formed at the distal end of the endoscope by connection of a resin tube to the distal end. A wire is connected to a position on the distal end of the endoscope or on the distal end of the resin tube, the position being radially offset from the center axis through which the endoscope is to be inserted. The endoscope is bent when the operator withdraws the wire. In another example of the structure, a resin tube is connected to the distal end of the endoscope, and a bend-recovery part formed from a coil spring or a like spring is attached to the distal end of the resin tube. In the case of the previously-described example, the wire is attached to the distal end of the endoscope, the distal end of the resin tube, or the distal end of the bend-recovery part. The endoscope is bent in a recovery manner when the operator withdraws the wire.

However, in such a structure, the wire is directly or indirectly fixed to the distal end of the endoscope. The force exerted to withdraw the wire also acts as force to withdraw the distal end of the endoscope, thereby compressing the insertion portion. Consequently, the insertion portion meanders or becomes contracted, thus resulting in a previously-described problem of the length of the insertion portion changing.

In this case, the distal end of the endoscope located within the endotracheal tube is withdrawn excessively far, and the interior wall of the endotracheal tube appears within the field of view of the endoscope, thus limiting the field of view of the operator and making it difficult for the operator to search an area of interest. The operator must control the amount by which the endoscope is to be inserted into the endotracheal tube so as to prevent the interior wall of the endotracheal tube from appearing within the field of view of the endoscope. Further, even when the amount has been properly readjusted, if the extent to which the endoscope is bent is diminished, the endoscope is extended, as a result of which the distal end of the endoscope sticks out from the endotracheal tube. In this event, blood or other substance adheres to the objective lens provided at the distal end of the endoscope, thereby rendering the endoscope unable to acquire images Performing such operations in an emergency situation is troublesome.

Another problem is that the insertion portion of the endoscope becomes twisted when the endoscope is bent. The endotracheal tube is given a tendency to bend in a certain direction, in order to facilitate intubation of the endotracheal tube into the patient's trachea. If the endoscope inserted in the endotracheal tube will not bend in the same direction in which the endotracheal tube tends to bend, the endotracheal tube may be intubated into an unexpected direction and fail to advance into the trachea, because the endotracheal tube is intubated while the endoscope serves as a guide.

In order to cope with such a problem, the endoscope is inserted into the endotracheal tube such that the direction in which the endotracheal tube tends to bend matches the direction in which the endoscope tends to bend. However, in some cases the endoscope does not bend in the direction in which it is normally bent. These cases include the case where the wire is slightly offset from the position where it is to be fixed, and the case where the residual torsion is present in a resin tube which serves as a sheath of the insertion portion. Since an elastic member used for the endotracheal tube or the endoscope-such as a resin tube or a coil spring-assumes a circular cross section, force for limiting torsion does not act on the elastic member. Since such an elastic member can bend in any direction, the previously-described problem inevitably arises.

Moreover, a portable endoscope for intubating an endotracheal tube to be used in combination with a compact power supply or light source has been conceived as an endoscope for quickly intubating the endotracheal tube into a patient's body at the scene of an accident or disaster.

In this portable endoscope, a compact lamp is used as the light source, and dry batteries or compact rechargeable batteries are used as the power supply. The light source and the power supply are incorporated into the operation portion or are removably attached to the outer sheath of the operation portion. In another type of endoscope, because even a compact power supply has a certain volume and weight, the power supply is provided separately from the endoscope, or both the power supply and the light source are separately from the endoscope. When the endoscope is in use, the power supply and the light source are connected to the operation portion by cables and are carried by or placed near the operator.

When the light source and the power supply are provided within the operation portion or removably attached to the outer sheath of the operation portion, consideration is given to determining locations for the light source and the power supply. If the light source and the power supply are provided in a grip of the operation portion, the grip will eventually become bulky for manual handling.

For this reason, the light source and the power supply are usually provided in a portion of the endoscope close to the operator.

Generally, an eyepiece section for optically observing the interior of the human body is provided at the portion of the endoscope close to the operator; i.e., the end of the operation portion, rather than at the grip. The light source and the power supply are usually provided in the vicinity of the eyepiece section.

When the light source and the power supply are provided at such a location and the operator holds the operation portion, the weight balance of the endoscope worsens, thus making the endoscope difficult to handle.

In the endoscope, an insertion portion to be inserted into the human body is connected to one end of the operation portion, and the eyepiece section is provided at the other end of the operation portion. The grip is usually provided at the portion of the operation portion close to the insertion portion rather than at the portion close to the eyepiece section.

The insertion portion is elongated and lightweight. If the eyepiece section is heavy, the endoscope is tilted toward the eyepiece section and the insertion portion is urged upward when the operator holds the grip. The endoscope is usually inserted into the patient from above while the patient is lying on his back.

Accordingly, the endoscope is to be inserted while the insertion portion is urged to face downward. However, because of weight balance, the insertion portion is urged to face upward, and the operator must forcefully hold the endoscope with his hand such that the insertion portion faces downward. The operator must continuously hold the endoscope in that state until intubation of the endotracheal tube is completed. This imposes great difficulty on the operator. Particularly, when the operator is performing delicate operation, holding the endoscope for a long period of time imposes great difficulty.

In the case of an endoscope—whose power supply and light source are provided separately from an operation portion and which is used while the power supply and the light source—are connected to the operation handle by a cable while the endoscope is carried by the operator, the cable hinders the operator's operation at the scene of an emergency where the operator and other personnel tend to move hurriedly and unpredictably. In a case where the operator carries the light source and the power supply, his clothing may be stained with gory hands when he attempts to remove the light source and the power supply after intubation of the endotracheal tube. In a case where the operator uses the endoscope while the light source and the power supply are situated near, the operator runs the risk of touching a contaminated area, such as a ground surface, or the light source or the power supply installed on the floor, with the result that the operator may intubate the endotracheal tube with contaminated hands.

SUMMARY OF INVENTION

The present invention has been conceived to solve the previously-described problem, and the object of the present invention is to provide an endoscope for intubating an endotracheal tube which enables an operator to perform a bending operation while directly feeling resistance against the endotracheal tube experiences while being intubated, by hand; which obviates a necessity for coordinated operation involving the danger of the endotracheal tube being pulled out, such as shifting of the operator's hand from an operation section to the endotracheal tube during intubation operation; and which enables safe, quick, and reliable intubation operation.

The present invention has been conceived to solve the previously-described problem, and another object of the present invention is to provide an endoscope for intubating an endotracheal tube which prevents the distal end of the endoscope from being compressed even when the endoscope is subjected to bending force, which prevents a change in the position of the distal end of the endoscope within the endotracheal tube, and which reliably provides a wide field of view.

Another object of the present invention is to provide an endoscope for intubating an endotracheal tube which is stably bent in a certain direction and capable of properly guiding the endotracheal tube.

The present invention has been conceived to solve the above-described problem, and the object of the present invention is to provide a portable endoscope for intubating an endotracheal tube which does not hinder an operator during intubation of an endotracheal tube at the scene of an emergency where the operator and other personnel tend to move hurriedly and unpredictably, which eliminates anxiety about contamination, and which enables easy, safe intubation of the endotracheal tube into the patient's body with good operability.

An endoscope for intubating an endotracheal tube according to the present invention is provided by comprising an elongated insertion portion including at least an image transmitting optical fiber bundle, an illumination light transmitting optical fiber bundle, and a bendable element;

an operation portion connected to the proximal end portion of the insertion portion;

a bending operation mechanism provided in the operation portion;

a bendable element for bending the insertion portion provided so as to extend from the inside of the insertion portion to the bending operation mechanism;

an endotracheal tube connection section provided in the vicinity of a joint between the insertion portion and the operation portion; and a bending operation piece which is provided in the bending operation mechanism and extends beyond the endotracheal tube connection section toward the distal end of the insertion portion.

In the endoscope of the present invention, the bending operation piece extends beyond the endotracheal tube connection section toward the distal end of the insertion portion. As a result, the operator can readily operate the bending operation piece of the bending operation mechanism with the fingers of the hand that is holding the endotracheal tube, thereby enabling the operator to bend the endoscope while holding the endotracheal tube directly with his hand. Accordingly, the operator can intubate the endotracheal tube while feeling, directly by hand, resistance against the endotracheal tube within the body cavity.

The operator can intubate the endotracheal tube while holding it with his hand. So long as the operator holds the laryngoscope in his left hand and intubates the endotracheal tube while holding the endotracheal tube equipped with the endoscope in his right hand, the endoscope can be withdrawn by an assistant in that state; namely, without the operator having to shift his hand from the operation section of the endoscope to the endotracheal tube in coordination with the assistant.

An endoscope for intubating an endotracheal tube according to the present invention is provided by comprising:

an elongated insertion portion which has a distal end portion and a proximal end portion and which includes at least an image transmitting optical fiber bundle and an illumination light transmitting optical fiber bundle;

an operation portion which is connected to the proximal end portion of the insertion portion;

a bending operation mechanism provided on the operation portion; and a bendable element which is provided so as to extend from the inside of the insertion portion to the bending operation mechanism and which bends the insertion portion, wherein the bendable element includes an elongated elastic member which has one end constituting a free end disposed in the vicinity of the distal end of the insertion portion within the same and whose other end is fixed to the proximal end portion of the insertion portion or the operation portion, and a push-pull element which has one end connected to the vicinity of the free end of the elastic member and the other end connected to the bending operation mechanism.

Preferably, the elastic member is formed from a thin plate.

Preferably, the push-pull element is formed from a thin plate.

In the endoscope of the present invention, the bendable element comprises an elongated elastic member which has one end constituting a free end in the vicinity of the distal end of the insertion portion within the same and whose other end is fixed to the proximal end portion of the insertion portion or the operation portion, and a push-pull element which has one end connected to the vicinity of the free end of the elastic member and the other end connected to the bending operation mechanism. By such a configuration, even if bending force is exerted on the endoscope as a result of the operator pulling the push-pull element, compression force stemming from the tensile strength of the push-pull element does not act on the distal end or insertion portion of the endoscope. Consequently, a reduction in the length of the insertion portion of the endoscope is prevented, and the distal end of the endoscope fitted into the endotracheal tube is prevented from being changed when the distal end is bent. So long as the endoscope is once fitted into an appropriate position within the endotracheal tube, the objective lens is prevented from being stained with blood and the endoscope can stably provide a wide field of view without interference from the interior wall of the endotracheal tube.

Further, the elastic member of the bendable element is formed from a thin plate. Even when the insertion portion of the endoscope is subjected to twisting action when bending force is exerted on the endoscope, the flat plate is bent in the thicknesswise direction but is difficult to bend in the widthwise direction. The force exerted in the direction in which the endoscope tends to bend acts as resistance against twisting action, whereupon the bending direction is maintained stably.

Moreover, the push-pull element of the bendable element is formed from a thin plate. Therefore, the resistance against twisting action is increased, whereupon the bending direction is maintained more stably.

An endoscope for intubating an endotracheal tube according to the present invention is provided by comprising:

an elongated insertion portion including at least an image transmitting optical fiber bundle, an illumination light transmitting optical fiber bundle, and a bendable element;

an operation portion which is connected to the proximal end portion of the insertion portion and includes a light source;

an endotracheal tube connection section which is provided in the vicinity of a joint between the insertion portion and the operation portion;

a bending operation mechanism having a bending operation piece which is provided on the operation portion and extends beyond the endotracheal tube connection section toward the distal end of the insertion portion; and a power supply provided in the bending operation piece.

In the endoscope for intubating an endotracheal tube according to the present invention, the light source and the power supply are provided in the operation portion of the endoscope. The endoscope of the present invention prevents a cable from interfering with the operator's operation, which would otherwise occur in the case of an existing endoscope whose power supply and light source are connected by a cable. Further, there can be diminished the chance of the operator touching a contaminated area and staining his clothing, and the operator can readily operate the endoscope with good sanitation.

The bending operation piece of the bending operation mechanism is provided so as to extend beyond the endotracheal tube connection section toward the distal end of the insertion portion, and the heavy power supply is provided within the bending operation piece.

As a result, when the endoscope is held by hand, the center of gravity of the endoscope is situated at the portion held by the hand or at a position closer to the insertion portion than to the portion held by hand. The insertion-side of the endoscope can be urged downward with application of a small amount of force or goes down without application of force. Therefore, the endoscope can be readily intubated into the patient's body. Since the endoscope does not require unwanted force, the operator can perform a delicate operation.

DETAILED DESCRIPTION OF PREFERRED EMBODIMENTS

Figure 1:
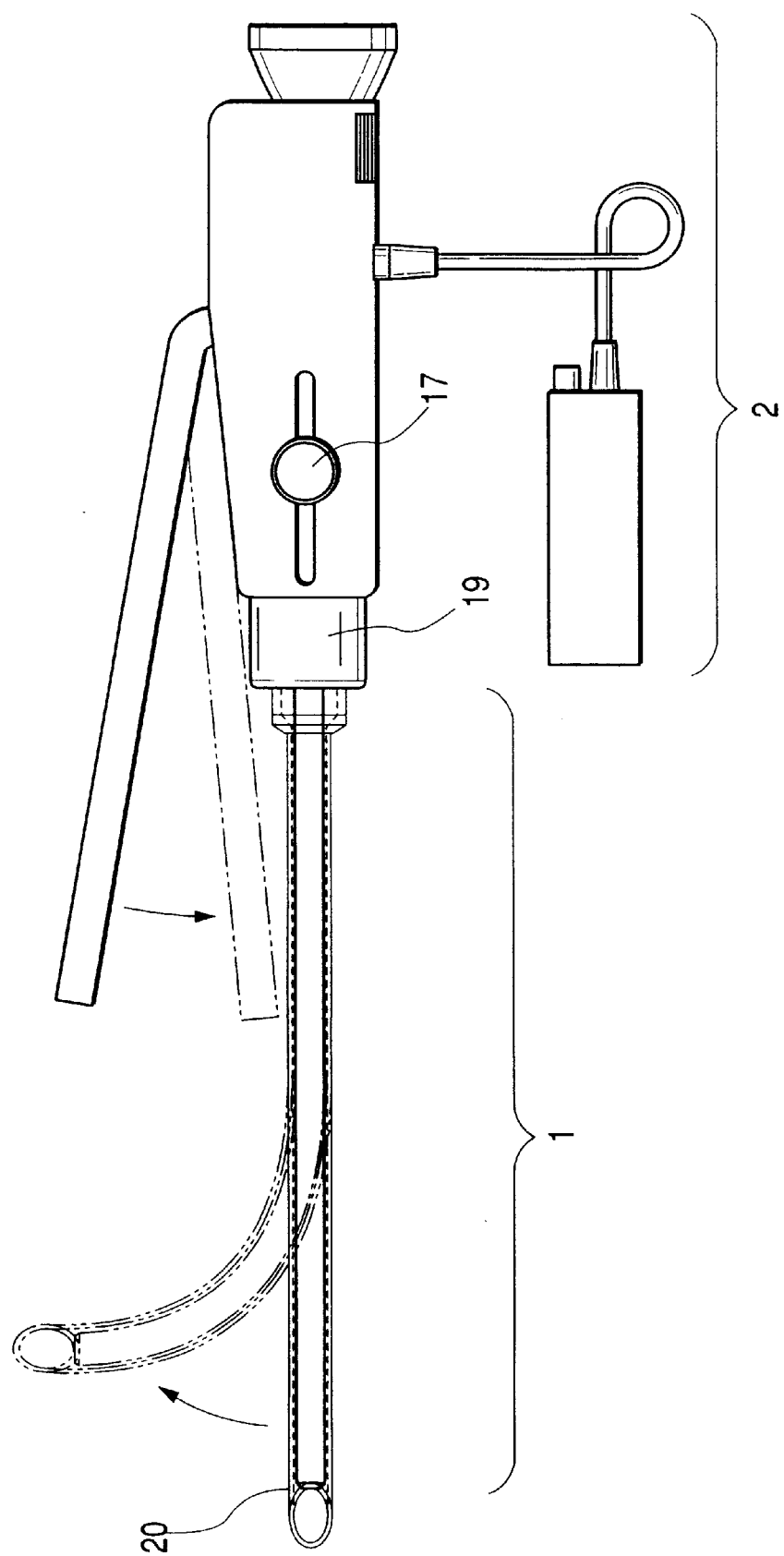
FIG. 1 is an illustration showing the entire configuration of an endoscope according to one embodiment of the present invention.

An embodiment of the present invention will be described hereinbelow by reference to the accompanying drawings. FIG. 1 is an illustration showing the overall configuration of an endoscope according to one embodiment of the present invention. The endoscope comprises an insertion portion 1 which is to be inserted into the internal space of an endotracheal tube 20; and an operation portion 2 which is connected to the proximal end portion of the insertion portion 1 and is disposed outside the endotracheal tube 20.

Figure 2:
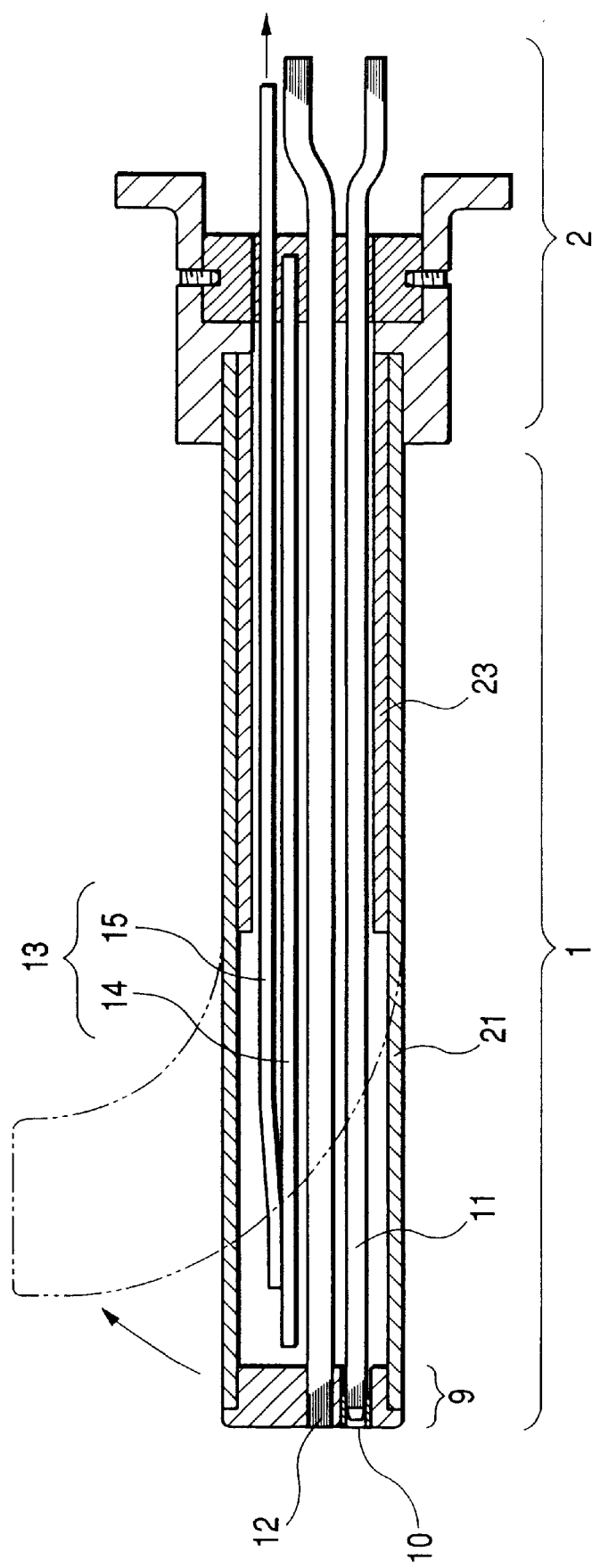
FIG. 2 is a cross-sectional view showing an insertion portion according to the embodiment.
Figure 3:
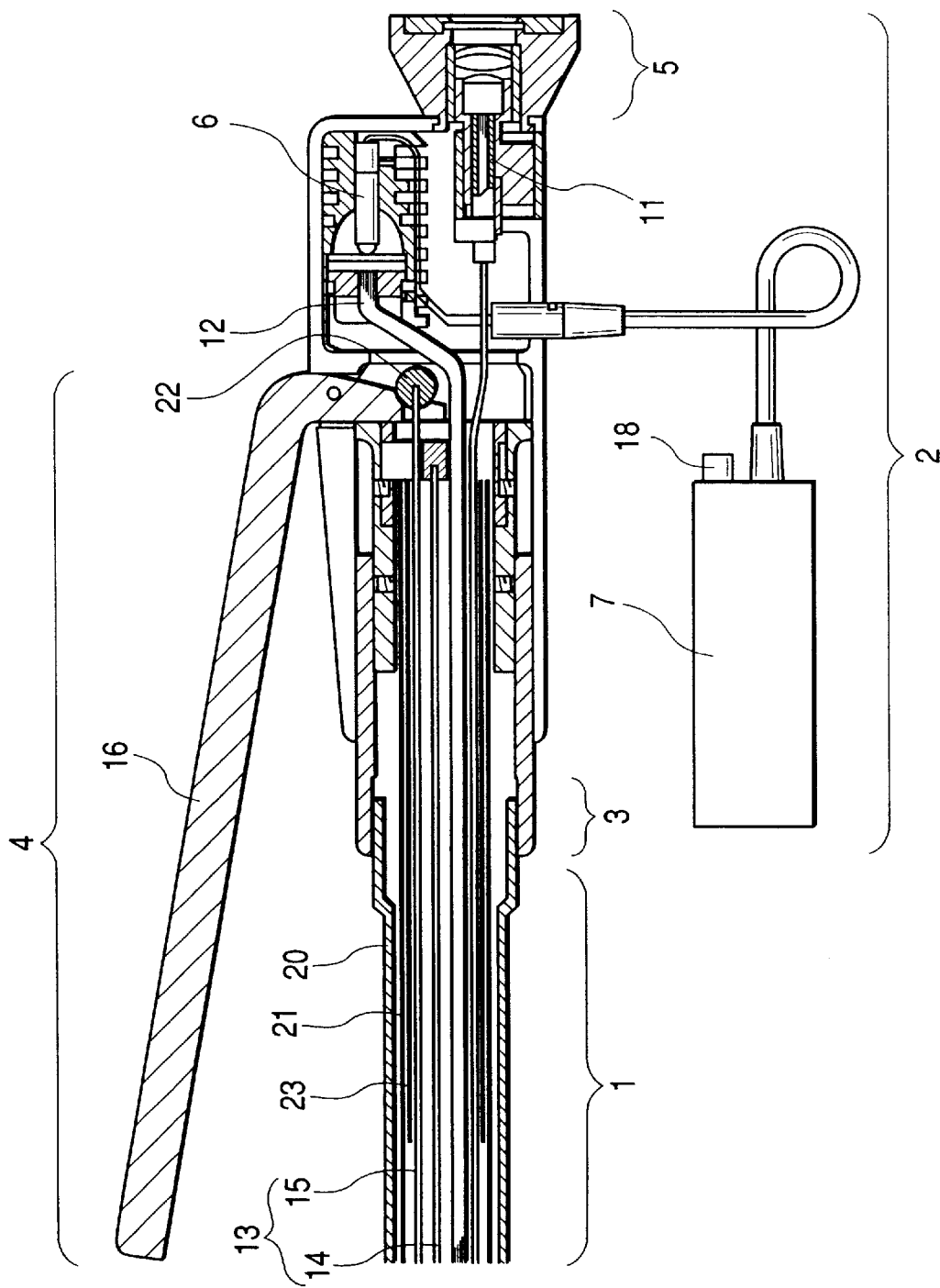
FIG. 3 is a cross-sectional view showing an operation portion according to the embodiment.

The detailed structure of the endoscope will be described by reference to FIG. 2, which is a cross-sectional view of the insertion portion 1, and FIG. 3, which is a cross-sectional view of the operation portion 2.

An endotracheal tube connection section 3 for securing the endotracheal tube 20 is provided in the vicinity of a joint between the operation portion 2 and the insertion portion 1. Moreover, the operation portion 2 is provided with a bending operation mechanism 4 for bending the insertion portion 1, and an eyepiece section 5 to be used for optically observing the interior of a body cavity.

Further, a light source 6 is housed in the operation portion 2 and is electrically connected to a power supply 7 by an electric cable. Power is supplied to the light source 6 by turning on a switch 18, to thereby illuminate the light source 6. Although in the present embodiment the power supply 7 is provided outside the handle operation section 2, the power supply 7 may also be provided within the operation portion 2.

The insertion portion 1 has an elongated shape, and a distal rigid portion 9 is provided at the end of the insertion portion 1. An objective lens 10 is fitted to the end face of the distal rigid portion 9. An image transmitting optical fiber bundle 11 and an illumination light transmitting optical fiber bundle 12 are housed in the insertion portion 1. The objective lens 10 is optically connected to the distal end of the image transmitting optical fiber bundle 11, and the proximal end portion side of the image transmitting optical fiber bundle 11 is optically connected to the eyepiece section 5. The distal end of the illumination light transmitting optical fiber bundle 12 is terminated at a position at or in the vicinity of the objective lens 10, and the proximal end portion side of the illumination light transmitting optical fiber bundle 12 is optically connected to the light source 6. Further, a bendable element 13 for bending the insertion portion 1 in a certain direction is provided within the internal space of the insertion portion 1. The distal end of the bendable element 13 is extended to an area in the vicinity of the hollow distal rigid portion 9 of the insertion portion 1. The bendable element 13 comprises an elastic member 14 whose proximal end portion is connected to the proximal end portion side of the insertion portion 1 and is formed from an elongated and sheet-like metal plate; and a push-pull element 15 which has one end connected to the vicinity of the distal end of the elastic member 14 and the other end connected to the bending operation mechanism 4, and which is formed from an elongated sheet-like metal plate. The distal end of the bendable element 13 constitutes a free end within the internal space of the insertion portion 1. In other words, the distal end of the bendable element 13 is not connected to any element constituting the insertion portion 1, such as the distal rigid portion 9. The proximal end portion of the elastic member 14 may be fixed to the operation portion 2 rather than to the proximal end portion of the insertion portion 1. Further, the push-pull element 15 may assume a linear shape such as a wire rather than a plate-like shape. Moreover, the elastic member 14 and the push-pull element 15 may be formed from metal rather than from resin.

Bending Operation Mechanism

In a joint between the push-pull element 15 and the bending operation mechanism 4, a terminal 22 is fixed to the end of the push-pull element 15, and the terminal 22 is engaged with a lever 16 of the bending operation mechanism 4 such that the terminal 22 is withdrawn toward the eyepiece section 5 when the lever 16 is gripped. In response to the gripping action, the push-pull element 15 is withdrawn toward the eyepiece section 5, and the distal end of the push-pull element 15 draws the distal end portion of the elastic member 14. Consequently, the elastic member 14 is bent, whereupon the insertion portion 1 is bent, thus bending the endoscope.

The proximal end portion of the elastic member 14 and the proximal end portion of the push-pull element 15 are covered with a reinforcement pipe 23 formed from metal, and the portions of the elastic member 14 and the push-pull element 15 that are not covered with the reinforcement pipe 23 bend.

The proximal end portion of the illumination light transmitting optical fiber 12 is tied in a bundle and is optically connected to a light source 6 provided in the operation portion 2. Power is supplied to the light source 6 from a power supply 7 provided in the operation portion 2 by way of a cable.

An endotracheal tube connection section 3 is provided in the vicinity of the joint between the insertion portion 1 and the operation portion 2. The endotracheal tube connection section 3 can move back and forth in the direction in which an endotracheal tube 20 is to be intubated, and can be made stationary at an arbitrary position, thereby enabling the position of the distal end of the endotracheal tube 20 to match the position of the distal end portion 9 of the endoscope.

Before use of the endoscope having the previously-described configuration, the direction in which the endotracheal tube 20 tends to bend is matched with the direction in which the endoscope is to bend. The insertion portion 1 of the endoscope is inserted into the internal space of the endotracheal tube 20, and the endotracheal tube 20 is connected to the endotracheal tube connection section 3.

By controlling the position of the endotracheal tube connection section 3, the position of the endotracheal tube 20 is adjusted such that the distal end portion 9 of the endoscope remains a slight distance short of the distal end of the endotracheal tube 20; more specifically, such that the distal section 9 of the endoscope remains a slight distance short of the distal end of the endotracheal tube 20 to such an extent that the internal wall of the endotracheal tube 20 does not appear within the field of view of the endoscope.

Subsequently, the endotracheal tube 20 is intubated into the patient's body from the mouth. The operator searches the larynx by moving the endotracheal tube 20 back and forth while observing the trachea through the eyepiece section 5 of the endoscope, or by bending the endoscope or reducing bending force to be exerted on the endoscope by actuating the lever 16 of the bending operation mechanism 4. When the larynx is found, the endotracheal tube 20 is moved toward the larynx until the endotracheal tube 20 enters the trachea to a point where it is not easily pulled out. Only the endoscope is withdrawn from the endotracheal tube 20, and an inhaler is connected to the endotracheal tube 20 in order to supply oxygen to the lungs, thus ensuring the patient's airway.

The endoscope is bent in the following manner. When the lever 16 of the bending operation mechanism 4 is gripped, the end of the lever 16 withdraws the terminal 22 engaging the end of the lever 16 toward the eyepiece section 5. Since the terminal 22 is engaged with the end of the push-pull element 15, the push-pull element 15 is withdrawn toward the eyepiece section 5 as a result of withdrawal of the terminal 22. The distal end of the push-pull element 15 is connected to the distal end of the elastic member 14, and the proximal end portion of the elastic member 14 is fixed to the proximal end portion of the insertion portion 1. Since the elastic member 14 is stationary, the elastic member 14 is bent as a result of withdrawal of the push-pull element 15. The elastic member 14 fitted into the insertion portion 1 is bent, whereupon the insertion portion 1 is forcefully bent or warped. The distal ends of the elastic member 14 and the push-pull element 15 are fixed to neither the distal end portion 9 of the insertion portion 1 not the resin tube 21 which acts as the sheath of the insertion portion 1, thus constituting free ends. Therefore, the withdrawal force exerted on the push-pull element 15 is not applied to the distal end portion 9 or the resin tube 21. More specifically, the distal end portion 9 is forcefully bent so as to assume the same shape as the elastic member 14 and the push-pull element 15 without being subjected to force for compressing the distal end portion 9 i.e., toward the direction in which the endotracheal tube 20 is to be intubated. By the withdrawal force exerted on the push-pull element 15, the insertion portion 1 is bent without being contracted.

During use of the endoscope having the previously-described configuration, the insertion portion 1 of the endoscope is inserted into the internal space of the endotracheal tube 20, to thereby fasten the endotracheal tube 20 to the endotracheal tube connection section 3. Subsequently, the fastening screw 17 is released to allow the cylindrical piece 19 to move back and forth, thus matching the position of the distal end of the endotracheal tube 20 with the position of the distal end of the endoscope. Subsequently, the fastening screw 17 is fastened again.

The switch 18 is turned on, to thereby illuminate the light source 6, and the endoscope is intubated into the patient's body.

The endoscope is inserted while a laryngoscope is held by the operator's left hand and the endotracheal tube 20 used in combination with the endoscope is held by the operator's right hand.

At this time, the operator's right hand holds not the operation portion 2 of the endoscope but the proximal end portion of the endotracheal tube 20; i.e., a position close to the portion of the endotracheal tube 20 fixed to the endotracheal tube connection section 3.

The grip 8 or the endotracheal tube 20 is held by, for example, the four fingers of the operator's right hand other than the forefinger, while the operator rests his forefinger on the bending operation lever 16. Since the bending operation lever 16 extends beyond the endotracheal tube connection section 3 toward the distal end of the insertion portion 1, the operator's right forefinger which holds the proximal end portion of the endotracheal tube 20 can be readily rested on the bending operation lever 16.

While the endoscope is held in the state mentioned previously, the patient's mouth is forcefully opened by the laryngoscope. The endotracheal tube 20 is intubated deep inside the throat by the action of lifting up the tongue while the operator observes the throat. When the endotracheal tube 20 has been intubated into a position which cannot be observed from the outside, the operator observes the inside of the throat and searches the larynx by bending or restoring the insertion portion 1 to its original state, by actuating the bending operation lever 16 with the forefinger while observing through the eyepiece section 5. The distal end of the endotracheal tube 20 is moved deep into the trachea from the larynx. When the distal end of the endotracheal tube 20 has reached a position a short distance inside the trachea, the endoscope is withdrawn by an assistant. Subsequently, the endotracheal tube 20 whose original elasticity is restored as a result of removal of the endoscope is inserted further into the trachea, and a cuff attached to the endotracheal tube 20 is expanded, to thereby prevent the endotracheal tube 20 from being pulled out.

Figure 4:
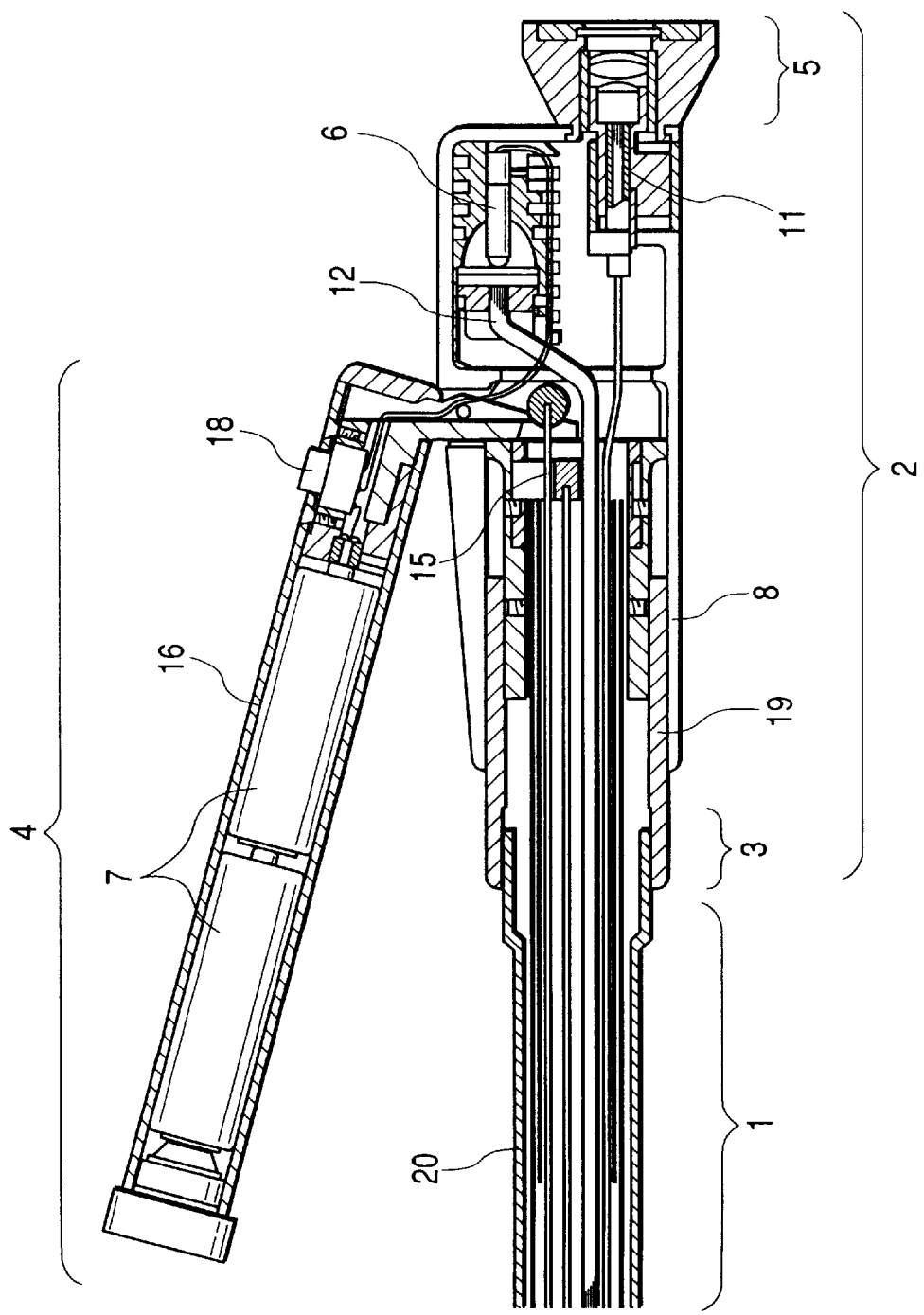
FIG. 4 is a cross-sectional view showing an operation portion according to another embodiment.

Further, FIG. 4 shows another improvement of the present invention.

A power supply 7 which enables replaceable housing of dry batteries is provided within the bending operation lever 16 as a power supply for illuminating the light source 6. The power supply 7 is electrically connected to the light source 6 by an electric cable. Power is supplied to the light source 6 by turning on a switch 18, thus turning on the light source 6. Rechargeable batteries serve as the batteries to be used as the power supply 7.

At this time, the endoscope achieves the following weight balance while being gripped.

The elongated insertion portion 1 is lightweight, and the operation portion 2 is considerably heavier than the insertion portion 1. Accordingly, when the insertion portion 1 and the grip 8 located in the vicinity of the endotracheal tube connection section 3 of the operation portion 2 are held, the portion of the endoscope in the vicinity of the heavy operation portion 2 is urged downward, whereas the portion of the endoscope in the vicinity of the lightweight insertion portion 1 is urged upward. At this time, since the heavy power supply 7 is provided in the bending operation lever 16 whose center of gravity is located at a position closer to the insertion portion 1 than to the grip 8 and which extends beyond the endotracheal tube connection section 3 toward the insertion portion 1, the center of gravity of the endoscope is located at a position closer to the insertion portion 1 than to the grip 8. As a result, the downward force exerted on the operation portion 2 is diminished; in other words, the insertion portion-side of the endoscope is urged downward, thereby diminishing the downward force which is exerted by the hand gripping the grip 8 on the insertion portion-side of the endoscope. The insertion portion-side of the endoscope is naturally urged downward when the operator simply holds the grip 8. Consequently, the endoscope can be readily tilted at an angle suitable for intubation into a patient who is lying on his back, from above. A necessity for exerting a force to operate the endoscope can be eliminated, thus greatly facilitating intubation of an endotracheal tube.

As has been described in detail, in the endoscope of the present invention, the bending operation piece extends beyond the endotracheal tube connection section toward the distal end of the insertion portion. As a result, the operator can readily operate the bending operation piece of the bending operation mechanism with the fingers of the hand that is holding the endotracheal tube, thereby enabling the operator to bend the endoscope while holding the endotracheal tube directly with his hand. Accordingly, the operator can intubate the endotracheal tube while feeling, directly by hand, resistance against the endotracheal tube within the body cavity. Consequently, the endotracheal tube can be safely intubated without involvement of a danger of damaging the wall of a body cavity, which would otherwise be caused by forceful insertion of the endotracheal tube.

The operator can intubate the endotracheal tube while holding it with his hand. So long as the operator holds the laryngoscope in his left hand and intubates the endotracheal tube while holding the endotracheal tube equipped with the endoscope in his right hand, the endoscope can be withdrawn by an assistant in that state; namely, without the operator having to shift his hand from the operation section of the endoscope to the endotracheal tube in coordination with the assistant. The endotracheal tube can be quickly and easily intubated without involvement of a risk of the endotracheal tube being pulled out, which would otherwise be caused by poor coordination during shifting of the operator's hand.

As has been described in detail, in the endoscope of the present invention, the bendable element, which is an elongated elastic member for bending the insertion portion, is provided such that the distal end of the elongated elastic member is not fixed to the distal end portion of the insertion portion of the endoscope, thus constituting a free end. By such a configuration, if bending force is exerted on the bendable element, the withdrawal force exerted on the bendable element does not act as force for compressing the distal end portion of the insertion portion, thereby preventing the distal end of the endoscope from retreating into the endotracheal tube equipped with endoscope, which would otherwise be caused by contraction of the insertion portion. Therefore, the present invention eliminates difficulty in searching an area of interest within the body cavity, which would otherwise be caused when the endoscope is receded by bending force and the internal wall of the endotracheal tube is caused to appear within the field of view of the endoscope.

Further, the elastic member of the bendable element is formed from a thin plate, and hence the elastic member is bent stably in a certain direction. Accordingly, the present invention can also eliminate difficulty in intubating an endotracheal tube into the trachea, which would otherwise be caused by a difference between the direction in which the endotracheal tube tends to bend and the direction in which the bendable element is to bend.

Moreover, the elastic member 14 and the push-pull element 15 of the bendable element are formed from thin plates, whereby the bending of the bendable element in a certain direction is made more stable.

As has been described in detail, in the endoscope for intubating an endotracheal tube according to the present invention, the light source and the power supply are provided in the operation portion of the endoscope. The endoscope of the present invention prevents a cable from interfering with the operator's operation, which would otherwise occur in the case of an existing endoscope whose power supply and light source are connected by a cable. Further, there can be diminished the chance of the operator touching a contaminated area and staining his clothing, and the operator can readily operate the endoscope with good sanitation.

The bending operation piece of the bending operation mechanism is provided so as to extend beyond the endotracheal tube connection section toward the distal end of the insertion portion, and the heavy power supply is provided within the bending operation piece. As a result, when the endoscope is held by hand, the center of gravity of the endoscope is situated at the portion held by hand or at a position closer to the insertion portion than to the portion held by hand. The insertion-side of the endoscope can be urged downward with application of a small amount of force or goes down without application of force. Therefore, the endoscope can be readily intubated into the patient's body. Since the endoscope does not require unwanted force, the operator can perform a delicate operation and safely intubate an endotracheal tube; in other words, an endotracheal tube can be safely intubated with good sanitation and with simple operation.

What is claimed is:

1. An endoscope comprising:
    an elongated insertion portion including at least an image transmitting optical fiber bundle,
    an illumination light transmitting optical fiber bundle, and
    a bendable element for bending the insertion portion provided so as to extend from the inside of the insertion portion to a bending operation mechanism;
    an operation portion connected to the proximal end portion of the insertion portion;
    said bending operation mechanism having a bending operation lever which is provided on the operation portion; and
    an endotracheal tube connection section provided in the vicinity of a joint between the insertion portion and the operation portion,
    wherein the bendable element includes:
        an elongated elastic member having a free end within the vicinity of the distal end of an interior of the insertion portion and another end fixed to the proximal end portion of the insertion portion or the operation portion, and
        a push-pull element having one end connected to the vicinity of the free end of the elastic member and another end connected to said bending operation mechanism;
    and wherein said bending operation lever engages said another end of said push-pull element and includes a power supply for providing electrical energy to a light source in said operation portion.

2. The endoscope as defined in claim 1, wherein the elastic member is formed from a thin plate.

3. The endoscope as defined in claim 1, wherein the push-pull element is formed from a thin plate.

4. An endoscope comprising:
    an elongated insertion portion including at least an image transmitting optical fiber bundle, and an illumination light transmitting optical fiber bundle;
    an operation portion connected to the proximal end portion of the insertion portion;
    a bending operation mechanism provided in the operation portion, including a bending operation piece which is provided on the operation portion;
    an endotracheal tube connection section provided in the vicinity of a joint between the insertion portion and the operation portion for securing an endotracheal tube; and
    moving means for moving said endotracheal tube connection section;
    wherein said endotracheal tube connection section is configured to be a cylindrical piece, said moving means comprising a key groove at said operation portion and a fastening screw through said key groove for allowing said cylindrical piece to move back and forth.

5. A method for inserting an endotracheal tube into the trachea of patient using endoscope comprising:
    an elongated insertion portion including at least
        an image transmitting optical fiber bundle,
        an illumination light transmitting optical fiber bundle;
    an operation portion connected to the proximal end portion of the insertion portion;
    a bending operation mechanism provided in the operation portion, including
        a bending operation piece which is provided on the operation portion;
        an endotracheal tube connection section configured to be a cylindrical piece and
    provided in the vicinity of a joint between the insertion portion and the operation portion for securing the endotracheal tube; and
    moving means comprising a key groove at said operation portion and a fastening screw through said key groove for allowing said cylindrical piece to move back and forth;
    wherein the method comprising:
        (a) inserting said elongated insertion portion into internal space of the endotracheal tube, and securing said endotracheal tube at said endotracheal tube connection section;
        (b) releasing said fastening screw and positioning said cylindrical piece with said endotracheal tube, and fastening said fastening screw;
        (c) intubating said endotracheal tube with said endoscope to trachea of patient.

* * * * *